US00PP34688P3

(12) United States Plant Patent
Perrault et al.

(10) Patent No.: US PP34,688 P3
(45) Date of Patent: Oct. 25, 2022

(54) HOP PLANT NAMED 'HBC 735'

(50) Latin Name: *Humulus lupulus*
Varietal Denomination: HBC 735

(71) Applicant: HOP BREEDING COMPANY, L.L.C., Yakima, WA (US)

(72) Inventors: Jason Perrault, Toppenish, WA (US); Eugene G. Probasco, Yakima, WA (US); Michael D. Ferguson, Yakima, WA (US); Scott Varnum, Ellensburg, WA (US); Jaime Avalos P., Granger, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 17/300,776

(22) Filed: Nov. 2, 2021

(65) Prior Publication Data

US 2022/0142030 P1 May 5, 2022

Related U.S. Application Data

(60) Provisional application No. 63/204,957, filed on Nov. 2, 2020.

(51) Int. Cl.
*A01H 5/08* (2018.01)
*A01H 6/28* (2018.01)
*A01H 6/00* (2018.01)

(52) U.S. Cl.
USPC ..... Plt./236
CPC ..... *A01H 6/00* (2018.05)

(58) Field of Classification Search
USPC ..... Plt./236
CPC ... A01H 5/08; A01H 5/02; A01H 5/00; A01H 6/28; A01H 6/00
See application file for complete search history.

*Primary Examiner* — June Hwu
(74) *Attorney, Agent, or Firm* — Svendsen Legal, LLC

(57) ABSTRACT

A new hop plant named 'HBC 735' is disclosed. 'HBC 735' is used for its exceptional and unique aromatic qualities, and is suitable for beer flavoring.

6 Drawing Sheets

Genus and species: *Humulus lupulus*.
Variety denomination: 'HBC 735'.

STATEMENT REGARDING FEDERALLY SPONSORED RESEARCH OR DEVELOPMENT

None

BACKGROUND OF THE INVENTION

HBC '735' is a product of a controlled breeding program carried out by the inventors in the Yakima Valley of Washington State. 'HBC '735' was one of several seedlings resulting from an open pollination cross made in 2010 with female parent HBC '463', an unpatented variety, and an unknown male parent. Seedling plants from this cross were planted in 2011 and screened for disease resistance and sex in a greenhouse and field nursery near Granger, Wash. A single plant of 'HBC 735' was selected in 2014. In 2015 'HBC 735' was asexually reproduced via softwood cuttings, and expanded to thirty (30) plants in an evaluation blocks near Toppenish, Wash. In 2019 'HBC 735' was further expanded to a one (1) acre test block near Moxee, Wash. with plants asexually reproduced via softwood cuttings. The 'HBC 735' plants have now been observed and evaluated for several years. Throughout several generations of asexual propagation, 'HBC 735' has been observed to retain its distinctive characteristics and remain true to type.

SUMMARY OF THE INVENTION

A new and distinct hop plant is described herein, with the 'HBC 735' cultivar characterized by having cones which are late-season maturing, and with a high alpha acid content. The new cultivar exhibits a lemony citrus aroma with piney and spicy notes, and some tropical aromas of cantaloupe and pineapple. The new cultivar is suitable for beer flavoring.

COMPARISON OF 'HBC 735' TO PARENT PLANT AND COMPARISON CULTIVAR

Table 1. below, sets forth some of the distinguishing characteristics of 'HBC 735' as compared to its female parent 'HBC 463', and to the 'Chinook' cultivar as a closely comparable cultivar.

TABLE 1

| | INSTANT CV. 'HBC 735' | FEMALE PARENT 'HBC 463' | COMPARISON CV. 'CHINOOK' |
|---|---|---|---|
| Alpha (% of cone weight) | 15.2-16.0 | 11-12 | 11.5-15 |
| Beta (% of cone weight) | 6.4-7.0 | 5.5-5.6 | 3-4 |
| Co-humulone (% of alpha acids) | 26.5-27.0 | 41-52 | 27-31 |
| Total Oil (mL/100 g) | 2.2-3.6 | 1.1-2.6 | 1.0-2.5 |

BRIEF DESCRIPTION OF THE PHOTOGRAPHS

Figure 1:
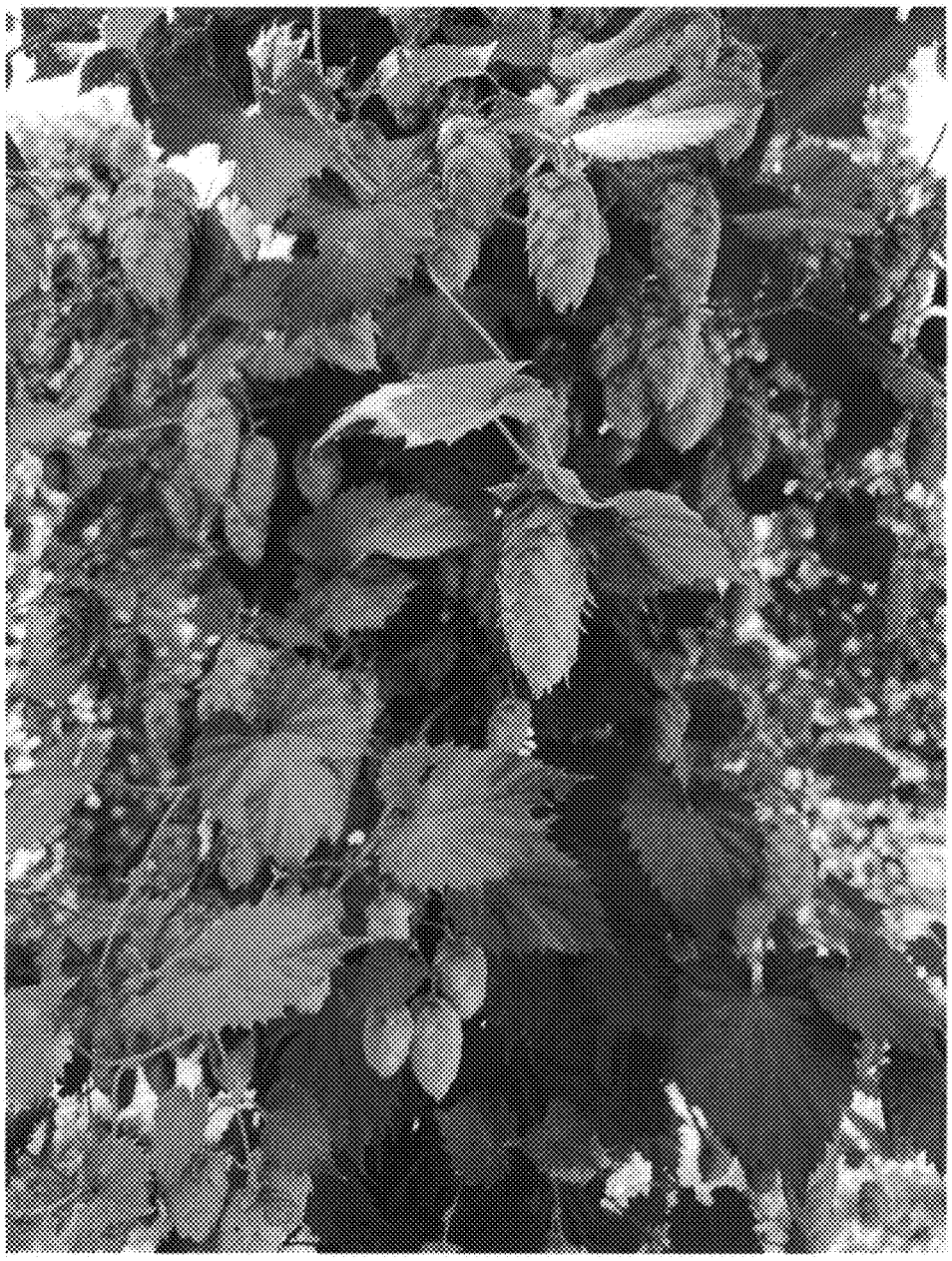
FIG. 1 illustrates a maturing 'HBC 735' hop plant as growing on a trellis.
Figure 2:
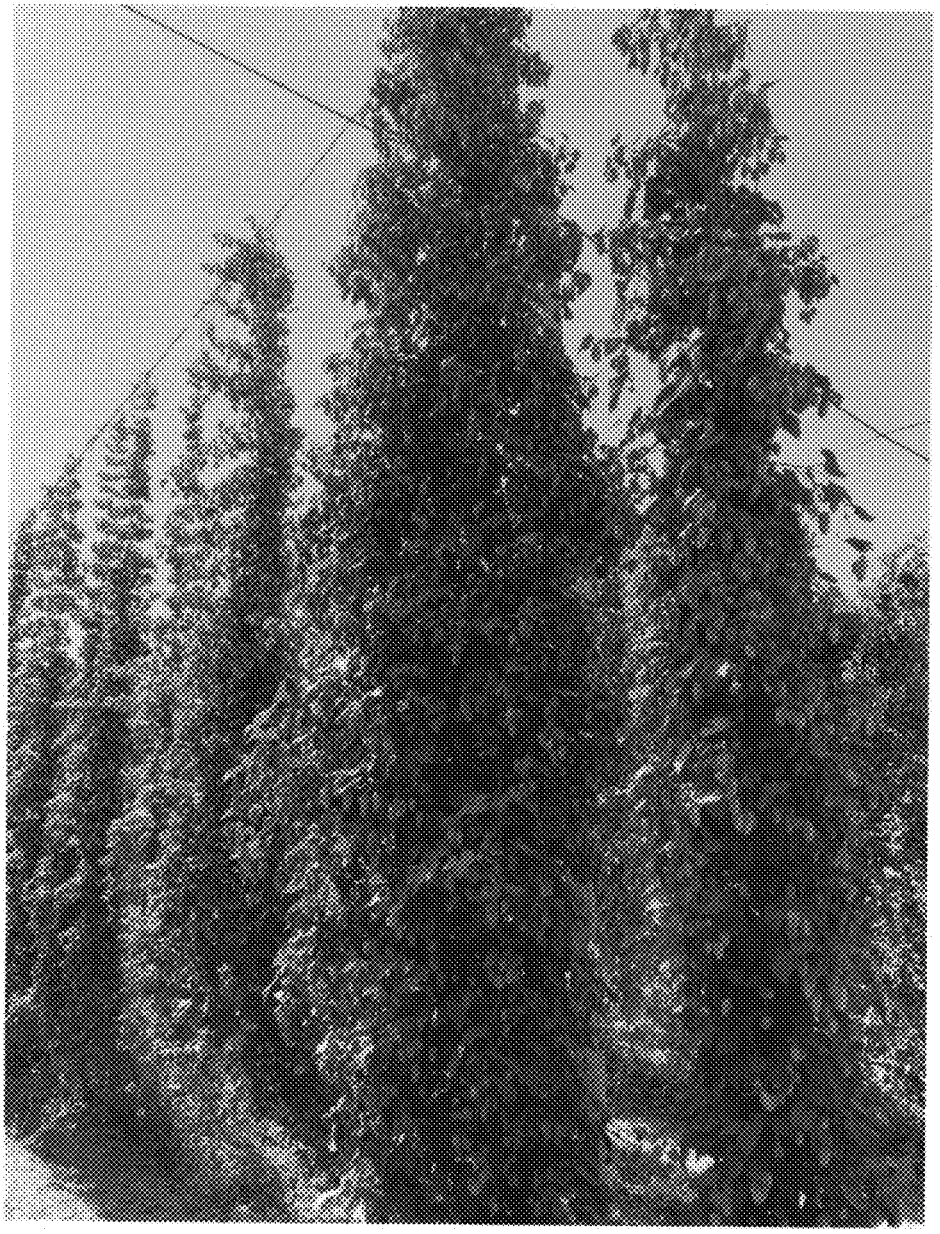
FIG. 2 illustrates a multiple of trellis with maturing 'HBC 735' hop plants.
Figure 3:
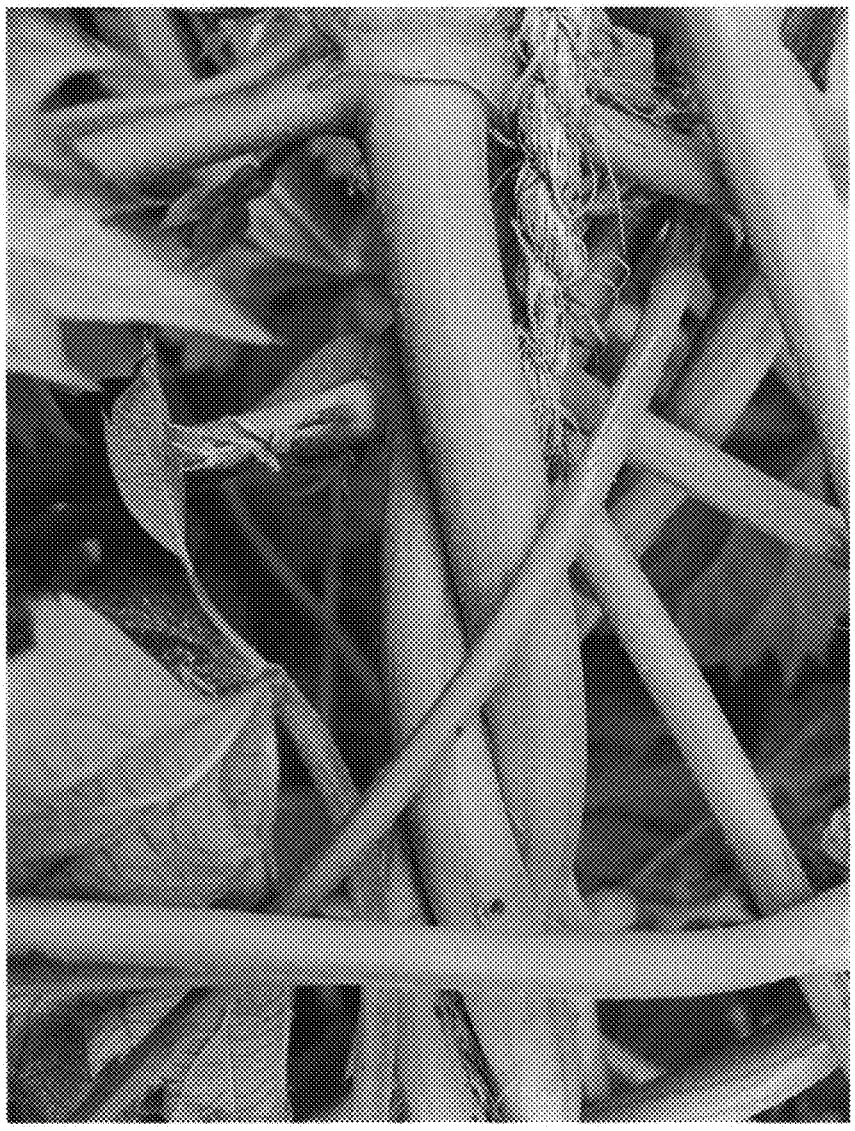
FIG. 3 illustrates bines of a mature 'HBC 735' hop plant as grown on a trellis.
Figure 4:
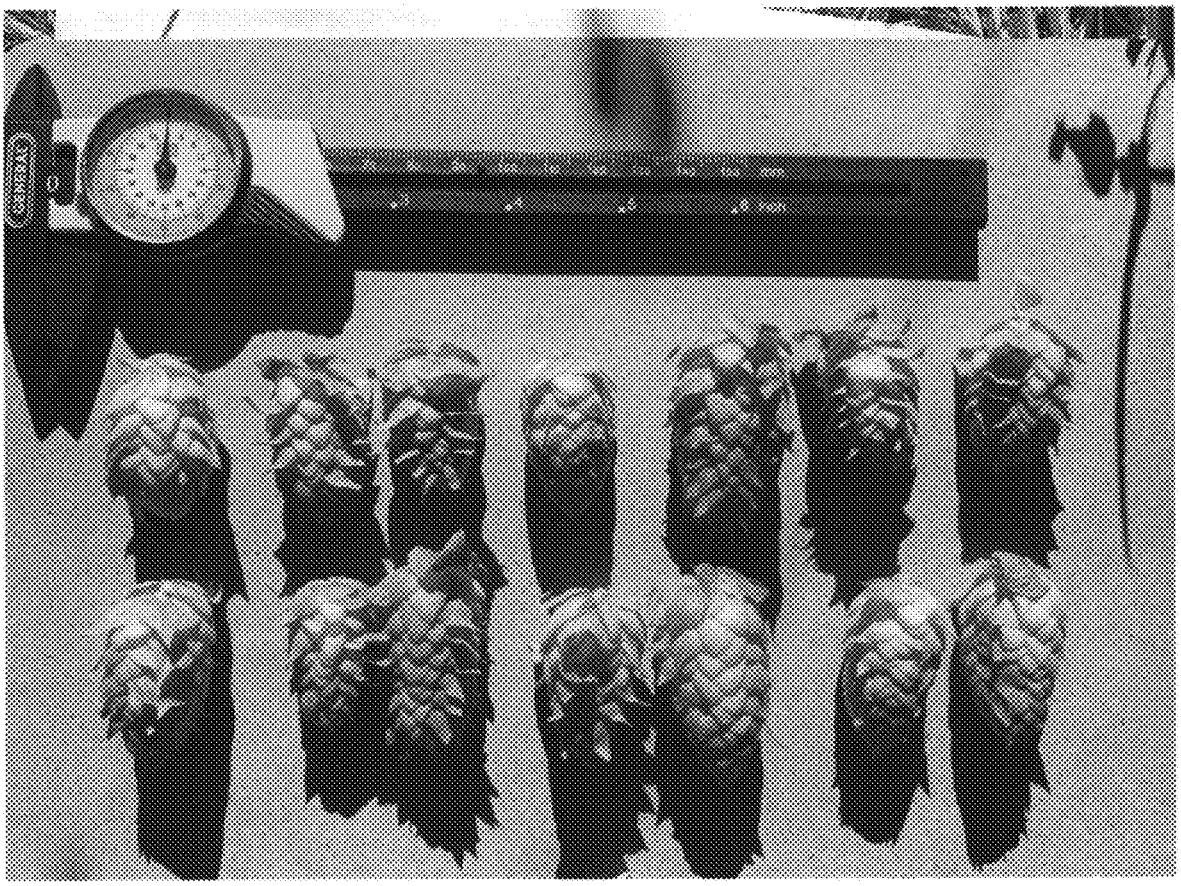
FIG. 4 illustrates whole mature cones of a 'HBC 735' hop plant.
Figure 5:
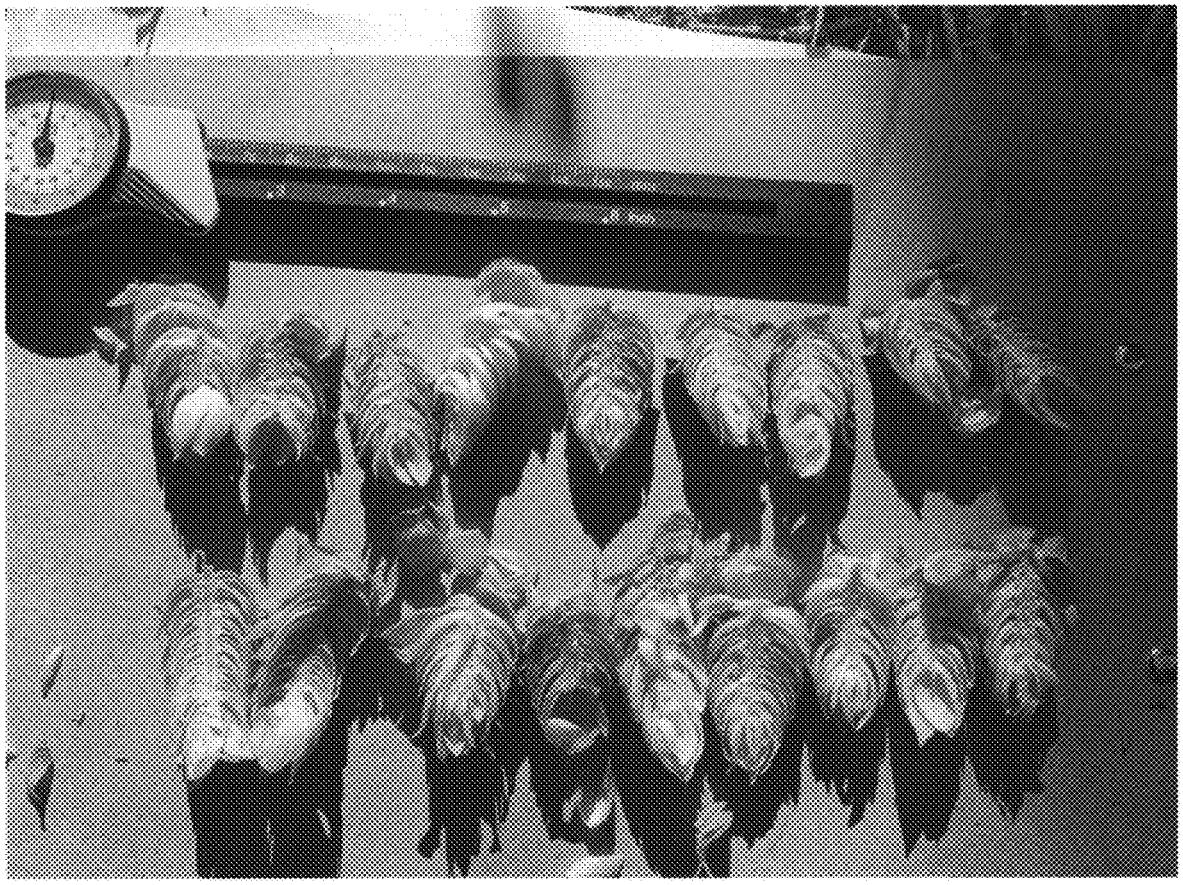
FIG. 5 illustrates cross sections of mature cones of a 'HBC 735' hop plant.
Figure 6:
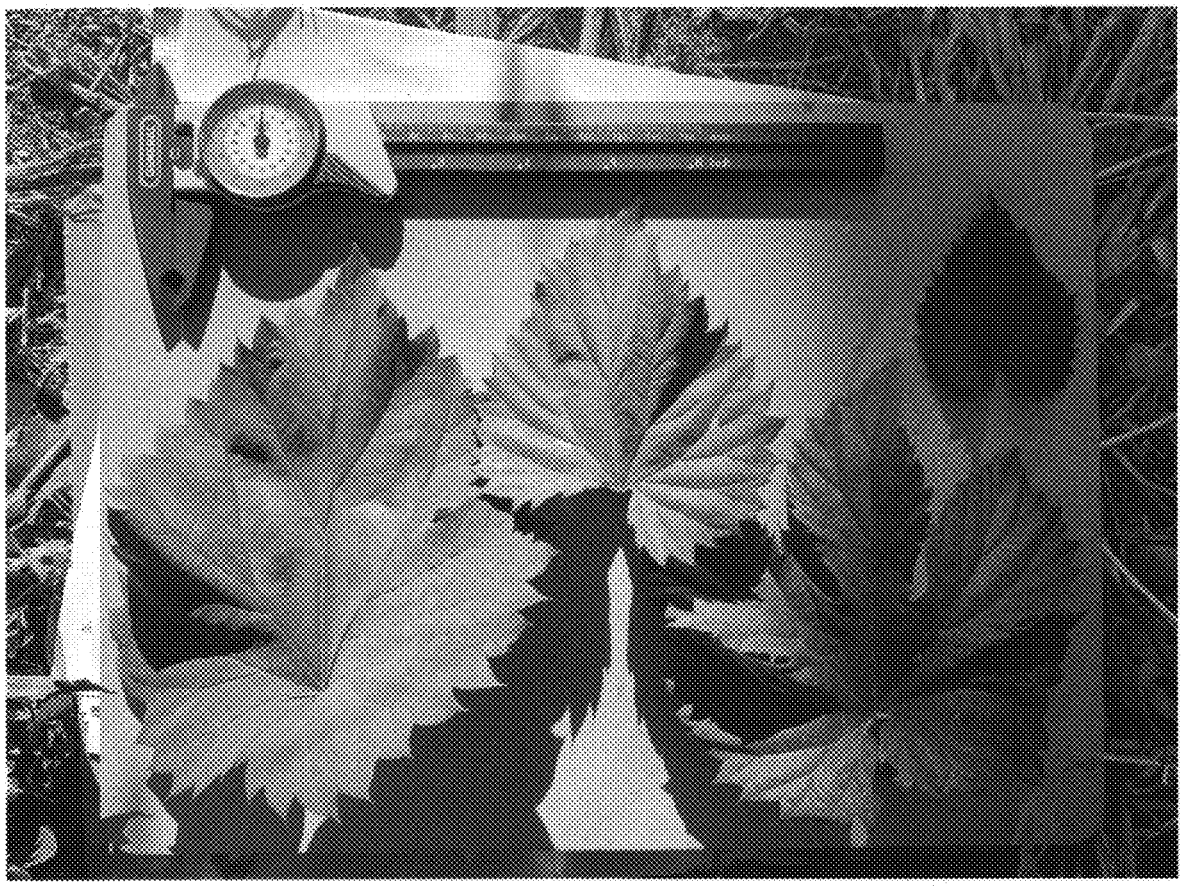
FIG. 6 illustrates a multiple of leaves of a maturing 'HBC 735' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made in during the 2017-2020 growing seasons at Toppenish, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. Color code designations are by reference to The R.H.S. Colour Chart, 4th ed., Copyright 2001, published by The Royal Horticultural Society of Great Britain.

Ploidy: Diploid.

Sex: Female.

Use: Brewing beer and ale.

Plant shape: Climbing bine, columnar growth.

Maturity/harvest date range (early, medium, late): Late.

Yield: Average yield is expected to be approx. 2,800 to 3,300 pounds per acre.

Hardiness: Observed Plant Hardiness Zone 7a.

Disease and pest resistance or susceptibility:

*Powdery mildew.*—Tolerant.

TABLE 2

| Oil Analytical Characteristics (Averages) | |
|---|---|
| % Alpha Acid (% cone weight) | 15.2 to 16.0 |
| % Beta Acid (% cone weight) | 6.4 to 7.0 |
| % Cohumulone (% alpha acids) | 26.5 to 27.0 |
| % Humulene (% of total oils) | 13.5 |
| % Caryphyllene (% of total oils) | 8.1 to 9.0 |
| % Farnesene (% of total oils) | 0.2 to 0.8 |
| % Linalool (% of total oils) | 0.4 |
| Total Oils (ml/100 g of cones): | 2.2 to 3.6 |

Aroma profile: Grassy, Herbal, Floral, Spicy, and Citrus.

Bine:

*Bine color.*—Yellow-Green 144B.
*Stripe present.*—Yes.
*Stripe color.*—Greyed-Purple 183C.
*Stipule direction.*—Up and Down.
*Stipule color.*—Yellow-Green 146B.
*Anthocyanin coloration on main bine.*—Very Weak.
*Average number of stipules per bine.*—127.
*Stipule shape.*—Small Triangular.
*Bine diameter.*—8.9 mm at base; 9.4 mm at nine feet; and 5.2 mm at terminal end of eighteen feet.
*Typical bine length.*—663 cm.
*Typical internode length* (*bine*).—20.8 cm.
*Typical internode length* (*lateral*).—11.0 cm.
*Average lateral length* (*on bottom third of plant*).—74.1 cm.
*Average lateral length* (*on middle third of plant*).—74.5 cm.
*Average laterals length* (*on upper third of plant*).—38.4 cm.
*Lateral density on middle third of plant* (*typical number of laterals present between nodes on bines*).—Medium (two laterals per node).

Leaf:

*Arrangement.*—Opposite.
*Shape.*—Palmate, Tripartite, Cordate.
*Apex.*—Acuminate.
*Base.*—Cordate.
*Average length of mature leaf.*—17.2 cm.
*Average width of mature leaf.*—16.6 cm.
*Color of mature leaf upper surface.*—Yellow-Green 147A.
*Color of mature leaf lower surface.*—Yellow-Green 147B.
*Leaf blistering on the upper side of leaf blade.*—Absent.
*Number of lobes.*—1 to 5.
*Margin.*—Serrate.
*Serrations per inch.*—3 to 5 (typically).
*Pose.*—Up and Down.
*Average petiole length* (*of mature leaf*).—127.3 mm.
*Average petiole diameter* (*of mature leaf*).—4.5 mm.
*Petiole color at base.*—Yellow-Green 144B.
*Venation.*—Palmate.
*Vein color.*—Yellow-Green 144B.

Cone:

*Avg. length.*—33.7 mm.
*Avg. diameter.*—18.6 mm.
*Cone shape.*—Ovate.
*Bract tip color.*—Yellow-Green 144A.
*Bract base color.*—Yellow-Green 149D.
*Bract shape.*—Orbicular.
*Bract length.*—15 mm.
*Bract width.*—12.7 mm.
*Bract tip shape.*—Cuspidate.
*Bract tip position.*—Curved upward and recurved-downward.
*Degree of bract opening.*—Slightly Open.
*Average number of cone per node.*—Varies Greatly — Moderate to Many.
*Bracteole color* (*lower surface*).—Yellow-Green 145D.
*Bracteole color* (*upper surface*).—Yellow-Green 145C.
*Bracteole shape.*—Oval.
*Bracteole length.*—17 mm.
*Bracteole width.*—10 mm.
*Lupulin glands shape.*—Peduncutlated oblong polyps.
*Lupulin glands number per cone.*—Varies greatly — Moderate to many.
*Lupulin glands color.*—Yellow 6C.
*Time of flowering.*—Mid to late July.

What is claimed:

1. A new and distinct variety of Hop plant named 'HBC 735', substantially as illustrated and described herein.

* * * * *